United States Patent
DiFoggio (10) Patent No.: US 7,173,239 B2
(45) Date of Patent: Feb. 6, 2007

(54) METHOD AND APPARATUS FOR DOWNHOLE QUANTIFICATION OF METHANE USING NEAR INFRARED SPECTROSCOPY

(75) Inventor: Rocco DiFoggio, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 285 days.

(21) Appl. No.: 10/798,686

(22) Filed: Mar. 11, 2004

(65) Prior Publication Data

US 2004/0178336 A1    Sep. 16, 2004

Related U.S. Application Data

(60) Provisional application No. 60/454,987, filed on Mar. 14, 2003.

(51) Int. Cl.
*G01V 5/08*  (2006.01)

(52) U.S. Cl. .................. 250/269.1; 250/268; 250/254; 250/253; 250/256; 250/255

(58) Field of Classification Search ............. 250/269.1, 250/268, 256, 255, 254, 253
See application file for complete search history.

(56) References Cited

U.S. PATENT DOCUMENTS

| | | | |
|---|---|---|---|
| 4,994,671 A | 2/1991 | Safinya et al. | |
| 5,892,586 A | 4/1999 | Thony et al. | |
| 5,939,717 A | 8/1999 | Mullins | |
| 6,274,865 B1 | 8/2001 | Schroer et al. | |
| 6,343,507 B1 * | 2/2002 | Felling et al. | 73/152.19 |
| 6,476,384 B1 * | 11/2002 | Mullins et al. | 250/269.1 |
| 2002/0105650 A1 | 8/2002 | Stuttard | |
| 2003/0062472 A1 | 4/2003 | Mullins et al. | |
| 2003/0106993 A1 | 6/2003 | Chen et al. | |
| 2004/0007665 A1 * | 1/2004 | DiFoggio et al. | 250/269.1 |
| 2004/0069942 A1 | 4/2004 | Fujisawa et al. | |
| 2004/0104341 A1 | 6/2004 | Betancourt et al. | |
| 2004/0145743 A1 | 7/2004 | Wilson et al. | |
| 2004/0178336 A1 | 9/2004 | DiFoggio | |
| 2004/0233446 A1 * | 11/2004 | Dong et al. | 356/409 |
| 2005/0018192 A1 * | 1/2005 | DiFoggio et al. | 356/418 |

FOREIGN PATENT DOCUMENTS

GB    2 334 097 A    8/1999

* cited by examiner

*Primary Examiner*—Otilia Gabor
*Assistant Examiner*—Christine Sung
(74) *Attorney, Agent, or Firm*—Madan, Mossman & Sriram, P.C.

(57) ABSTRACT

The present invention describes a unique method and apparatus for applying near-infrared spectroscopy to estimate weight percent of methane in crude oil from which one can then infer gas-oil ratio (GOR) of crude oils downhole in real time while collecting a fluid sample. The correlation equations provided by this invention use two wavelengths, one centered at 1670 and the other centered at 1682 nm. Both wavelengths are primarily sensitive to the methane peak absorption. To significantly improve the fit, non-spectroscopic parameters, such as temperature or pressure, can be included in the correlation equation. Also, this invention can be used to monitor sample cleanup by monitoring the increase in GOR associated with cleanup as a fluid being pumped from the formation transitions from mostly gas-free filtrate to mostly gas-containing crude oil.

30 Claims, 6 Drawing Sheets

**Equations Correlating Weight Fraction Methane
in Mixtures of Crude Oil and Methane
to Optical Absorbance and Temperature**

Methane Weight Fraction = METHWTF = B0 + B1 * Var1 + B2 * Var2 + B3 * Var3 + B4 * Var4 ...

SQ70-82 = SQUARE(Absorbance_at_1670_nm - Absorbance_1682_nm)
SRSA1670 = SQRT(Absorbance_at_1670_nm)
SRSA1682 = SQRT(Absorbance_at_1682_nm)
TEMP_C = Temperature in Degrees Centigrade
TEMP_SQR = Square of Temperature in Degrees C Regression Summary for Dependent Variable: METHWRF
R = .98093203  $R^2$ = .96222765  Adjusted $R^2$ = .96151158
F(4,211) = 1343.8  p<0.0000  Std. Error of estimate: .04992

|  | B |
|---|---|
|  | 0.06514 = B0 = Intercept |
| Var1 = SQ70-82 | 11.1756 = B1 |
| Var2 = TEMP_C | 0.00087 = B2 |
| Var3 = SRSA1670 | -2.66167 = B3 |
| Var4 = SRSA1682 | 2.63245 = B4 |

Regression Summary for Dependent Variable: METHWRF
R = .98190316  $R^2$ = .96413381  Adjusted $R^2$ = .96327986
F(5,210) = 1129.0  p<0.0000  Std. Error of estimate: .04876

|  | B |
|---|---|
|  | 0.03143 = B0 = Intercept |
| Var1 = SRSA1670 | 2.53111 = B1 |
| Var2 = SRSA1682 | -2.55766 = B2 |
| Var3 = SQ70-82 | 11.9135 = B3 |
| Var4 = TEMP_C | 0.0019 = B4 |
| Var5 = TEMP_SQR | -6.2E-06 = B5 |

**Equation for Optical Absorbance per mm of
Methane as a Function of Density and Wavelength
at 11 nm FWHM, Center λ range of 1668-1684 nm,
for 100-30,000 psia and 75-200 C,**
is fitted by  Adj. $R^2$ = .94145159

| B | |
|---|---|
| -19.9061 = Intercept | |
| Methane Density  0.7747 | for Density in g/cc |
| WaveNumber/1000  3.3326 | |

**Equation for Density of Methane [g/cc] as
a Function of Pressure and Temperature
from 100-30,000 psia and 75-200 C**
is fitted by  Adj. $R^2$ = .99911359

|  | B |  |
|---|---|---|
|  | 2.771E-03 = Intercept |  |
| P | 2.480E-05 | for Pressure in psi |
| $P^2$ | -1.120E-09 |  |
| $P^3$ | 1.808E-14 |  |
| $T^2$ | -1.308E-07 | for Temperature in C |
| (P/T) | 1.455E-03 |  |
| $(P/T)^2$ | -4.922E-06 |  |
| $(P/T)^3$ | 5.934E-09 |  |

Equations Relating Gas Oil Ratio, GOR, to Weight Fraction of Methane, $f_M$, and Stock Tank Density, $\rho_O$, of Oil

1 bbl = 0.159 $m^3$ = 5.615 cu ft = 42 U.S. gal
1 Standard Cubic Foot (SCF) or Methane Gas at 14.7 psia & 60°F is 0.042358 lbs = 19.21327 grams.
Density of Methane at 60°F and 14.7 psia is 0.0006787 gr/cc = 0.04258 lbm/$ft^3$
Letting V = Volume, W = Weight, $\rho$ = Density, and using subscripts M for Methane and O for Oil,
GOR = $V_{Methane}$[SCR] / $V_{Oil}$[bbls] = {$W_M$ / (19.21 g/SCF)} / {($W_O/\rho_O$) (1 bbl/158.983 cc)}
Letting $f_M$ = Weight Fraction of Methane,
GOR = 8274.62 $\rho_O$ / (1/$f_M$ -1)
$f_M = W_M / (W_M + W_O) = \rho_M V_M / (\rho_M V_M + \rho_O V_O)$ so $W_O = W_M / (1/f_M - 1)$ which substitutes into above.
$f_M = 1/(1 + 8274.62 * \rho_O / GOR)$ where $W_G$ and $W_O$ are in grams, $\rho_O$ is in g/cc, and $f_M$ = Wt. Frac. of Methane

METHOD AND APPARATUS FOR DOWNHOLE QUANTIFICATION OF METHANE USING NEAR INFRARED SPECTROSCOPY

CROSS REFERENCE TO RELATED APPLICATIONS

This patent application claims priority from U.S. provisional patent application No. 60/454,987 filed on Mar. 14, 2003 entitled "A Method and Apparatus for Downhole Quantification of Methane Using Near Infrared Spectroscopy" by Rocco DiFoggio.

FIELD OF THE INVENTION

The invention relates generally to a method and apparatus for quantifying the weight percentage of methane or the gas oil ratio for a crude oil sample downhole by using the sample's absorbance at two specially selected optical channels. The center wavelengths and bandwidths of these channels were selected by a complex simulation.

BACKGROUND OF THE INVENTION

In wellbore exploration, typically drilling mud such as oil-based mud and synthetic-based mud are used. Filtrates from these muds generally invade the hydrocarbon bearing formation through the borehole wall. Thus, samples taken from the formation contain drilling mud filtrate contamination. Thus, a sufficient volume of fluid must pumped from the formation to reduce the filtrate contamination in the sample to an acceptable level. Open-hole sampling is an effective way to acquire representative formation fluid samples. Formation fluid sample acquisition and analysis allows determination of critical information for assessing the economic value of reserves. In addition, optimal production strategies can be designed to handle these complex fluids. In openhole sampling, initially, the flow from the formation contains a considerable quantity of filtrate, but as filtrate is drained from the formation, the flow increasingly becomes richer in formation fluid and less filtrate appears in the flow. That is, the composition of fluid flowing from the formation progresses towards a higher percentage of native formation fluid but a lower percentage of filtrate as pumping continues and the filtrate that had invaded the formation is depleted.

Thus, fluid being pumped from a wellbore undergoes a clean-up process in which the purity of the sample increases over time as filtrate is gradually removed from the formation so that less filtrate appears in the sample. As the composition of the sampled formation fluid changes, so do the optical and physical properties of the sampled fluid, such as optical absorption, fluorescence, refractive index, density, and viscosity. A number of different measurements are used to determine various optical and physical properties of a fluid downhole in real time. Measuring these properties of the fluid therefore provides insight into a sample's purity.

When extracting fluids from a formation, it is desirable to quantify the cleanup progress, that is, the degree contamination from filtrate in the formation fluid sample in real time. If it is known that there is too much filtrate contamination in the sample (e.g., more than about 10% filtrate), then there is little reason to collect a formation fluid sample in a sample tank. One should wait until the contamination level drops to an acceptable level. On the other hand, if by pumping for a relatively long time, it is possible to achieve an only slightly better filtrate contamination level, an operator may end up wasting very expensive rig time and also risks the very costly possibility of allowing a tool to become stuck in the wellbore.

When pumping first begins, the fluid being pumped contains a large amount of mud filtrate contamination but the fluid filtrate percentage is decreasing at the fastest rate. This process of decreasing fluid filtrate contamination is referred to as sample clean up. Later, the pumped fluid contains less contamination but the fluid filtrate percentage decreases at a slower rate. One way to monitor cleanup is to monitor the increase in gas oil ratio (GOR) as pumping continues and the flow from the formation cleans up from mostly gas-free oil-based mud filtrate and to mostly gas-containing oil. Oil companies are also very interested in knowing the GOR of the crude oils that they find downhole independent of using GOR as a cleanup monitor. Thus, there is a need for a method and apparatus for determining GOR in real time downhole.

SUMMARY OF THE INVENTION

This method and apparatus of the present invention utilizes spectroscopy to estimate the weight fraction of methane and the corresponding Gas Oil Ratio (GOR) for a methane-in-crude-oil mixture. A method and apparatus are provided to determine the gas oil ratio from the weight fraction of methane, which is determined spectroscopically. The present invention provides a method and apparatus for optical analysis of formation fluids using near infrared (NIR) illumination, which provides a measurement of optical absorbance at wavelengths of 1670 nanometers and 1682 nanometers. The methods of this invention correlate the absorption at these two wavelengths to the weight percent methane and GOR. A borehole apparatus for measuring the spectral absorbance of formation fluids includes a testing region, a conduit for directing formation fluid into the testing region, a light source emitting at least near infrared rays into the testing region, a spectral detector optically coupled to the testing region, and a processor coupled to the spectral detector. The testing region is an optically transparent cell or chamber which is located between the light source and the spectral detector such that light directed from the light source to the spectral detector is passes through formation fluid. The spectral detector is in one example is a filter spectrograph, which measures the spectrum of the light which has been transmitted through the formation fluid in the testing region.

The present invention provides a method and apparatus for quantifying methane and GOR downhole using a complex simulation and regression selection process to obtain specially selected optical filters having particular selected center wavelengths and bandpasses (11 nm full width half maximum FWHM) to quantify the weight percentage of methane or the GOR for a crude oil sample in real time downhole. Specifically, the invention is a method of determining weight percent methane and GOR for formation fluid samples being pumped from a formation surrounding a wellbore by a wireline tool or a monitoring-while-drilling formation tester to obtain weight percent methane and to estimate GOR for a formation fluid sample.

Unlike Mullins U.S. Pat. No. 6,476,384 (Mullins '384), which describes a method for determining GOR based on two wavelengths, the first located near a methane-gas spectral peak and the second located near a liquid-hydrocarbon spectral peak (representing oil), the present invention uses two wavelengths that are both near a single spectral peak for methane (i.e., two regions of the same methane peak). Also, unlike Mullins '384, which based its spectral GOR determination equations on a training set of binary mixtures of n-heptane (representing oil) and methane, the present invention bases its spectral GOR equations on synthetic mixtures of methane and dead crude oils. A dead crude oil is one for which little or no gas remains in the crude oil because it was not stored under pressure and therefore the gas in it was released. Unlike heptane, which is visibly clear, real crude oils have considerable amounts of dark-colored asphaltenes. The tails of the optical absorption peaks of asphaltenes usually produce the equivalent of a baseline offset and some baseline tilt in the long-wavelength region (1620–1780 nm) that includes both the methane and liquid hydrocarbon peaks. Also, the liquid hydrocarbon peak is more complicated (has features associated with aromatics, saturates, etc.) for the case of a mixture of hundreds of hydrocarbons (dead crude oils) than for the case of a single pure solvent (the saturate, n-heptane). For both reasons, in contrast to Mullins '384, the present invention uses stock tank crude oils rather than n-heptane to represent downhole crude oil in the modeling for GOR or weight percent methane.

BRIEF DESCRIPTION OF THE FIGURES

Other objects and advantages of the invention will become apparent upon reading the following detailed description and upon reference to the accompanying drawings in which:

FIG. 6 is illustration of a regression analysis over two wavelengths and temperature for weight percent methane and GOR.

DETAILED DESCRIPTION OF AN EXEMPLARY EMBODIMENT

Figure 1:
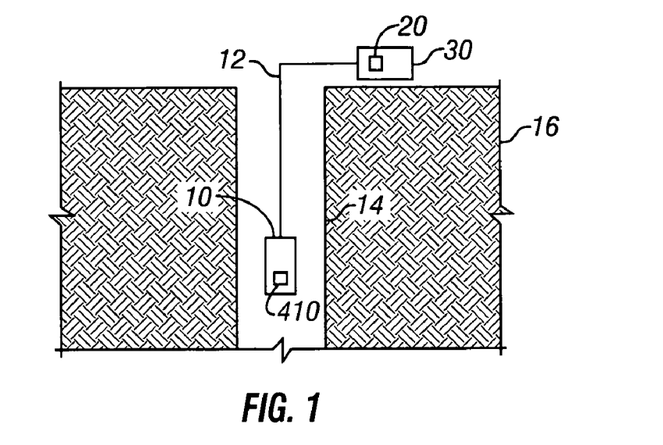
FIG. 1 is a schematic diagram of a exemplary embodiment of the present invention deployed on a wireline in a downhole environment.
Figure 2:
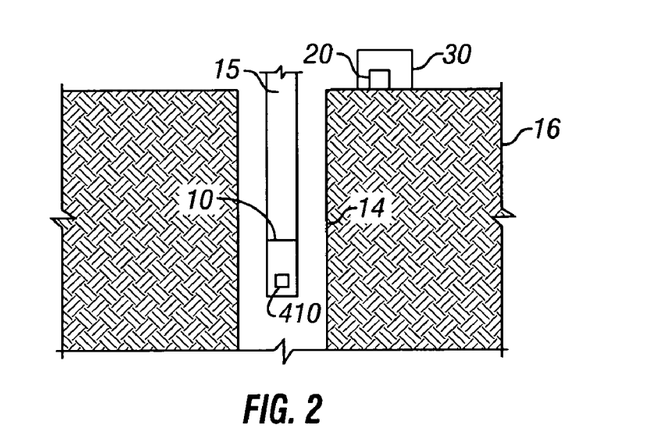
FIG. 2 is a schematic diagram of an exemplary embodiment of the present invention deployed on a drill string in a monitoring while drilling environment.
Figure 3:
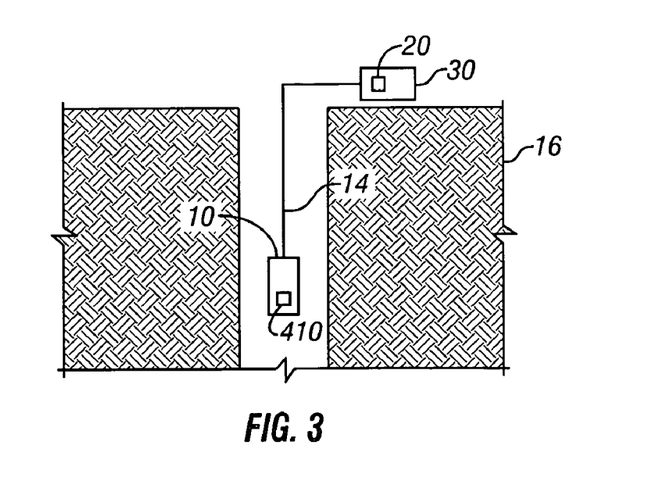
FIG. 3 is a schematic diagram of a exemplary embodiment of the present invention deployed on a flexible tubing in a downhole environment.

FIG. 1 is a schematic diagram of an exemplary embodiment of the present invention deployed on a wireline in a downhole environment. As shown in FIG. 1, a downhole tool 10 containing a optical analyzer 410 of the present invention is deployed in a borehole 14. The borehole is formed in formation 16. Tool 10 is deployed via a wireline 12. Data from the tool 10 is communicated to the surface to a computer processor 20 with memory inside of an intelligent completion system 30. FIG. 2 is a schematic diagram of a exemplary embodiment of the present invention deployed on a drill string 15 in a monitoring while drilling environment. FIG. 3 is a schematic diagram of an exemplary embodiment of the present invention deployed on a flexible tubing 13 in a downhole environment.

Figure 4:
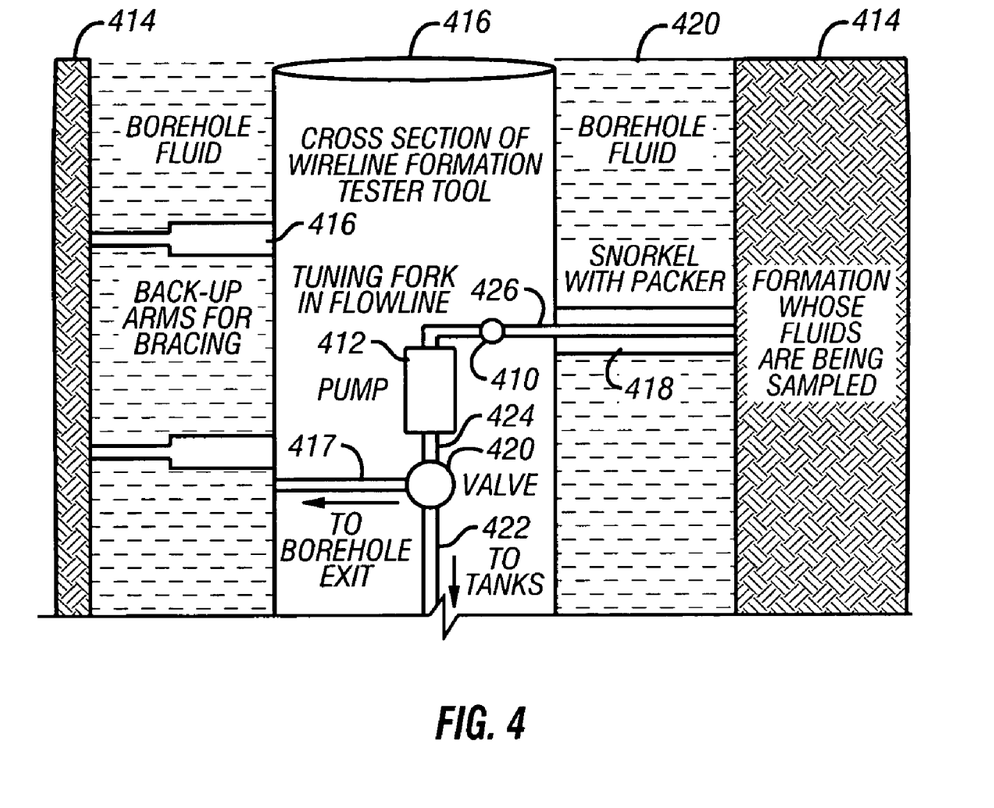
FIG. 4 is a schematic diagram of an exemplary embodiment of the present invention as deployed in a wireline downhole environment showing a cross section of a wireline formation tester tool.

FIG. 4 is a schematic diagram of an exemplary embodiment of the present invention as deployed from a wireline downhole environment showing a cross section of a wireline formation tester tool. As shown in FIG. 4, the tool 416 is deployed in a borehole 420 filled with borehole fluid. The tool 416 is positioned in the borehole by backup arms 416. A packer with a snorkel 418 contacts the borehole wall for extracting formation fluid from the formation 414. Wellbore fluid can be drawn from the wellbore also by not extending the snorkel to the wall and pumping fluid from the wellbore instead of the formation. Tool 416 contains optical analyzer 410, shown in FIG. 5, disposed in flow line 426. The optical analyzer response is monitored to determine weight percent methane and GOR of the formation fluid. Pump 412 pumps formation fluid from formation 414 into flow line 426. Formation fluid travels through flow line 424 into valve 420, which directs the formation fluid to line 422 to save the fluid in sample tanks or to line 418 where the formation fluid exits to the borehole.

Figure 5:
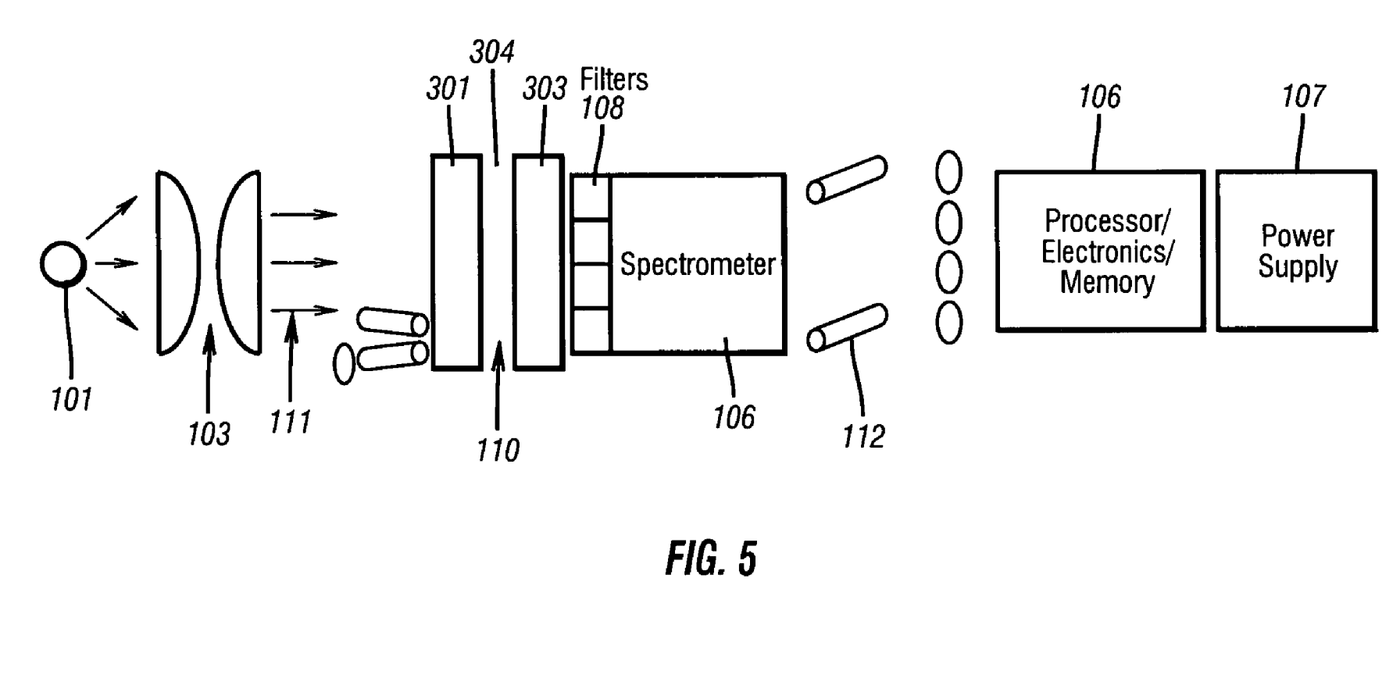
FIG. 5 is a diagram of the Fluid Characterization Module.

FIG. 5 illustrates a schematic representation for a downhole fluid characterization module, as, for example, the Baker Atlas SampleViews$^{SM}$ tool. A light source 101 (e.g. tungsten light bulb) emits light toward a formation or wellbore sample 110. Light from light source 101 is collimated by a collimating lens device 103 lying between the light source and the sample 110. The collimated light 111 is incident generally perpendicular to a first sapphire window 301 adjacent sample 110. Sapphire windows 301 and 303 lie generally perpendicular to the collimated beam of light and are separated by a gap or channel 304 enabling a fluid sample 110 to flow between them. The flow channel 304 can be flow line 426. Reflected and fluoresced light can be monitored over time in the spectrometer 105 and processor/electronics/memory 106 comprising a central processing unit, control circuitry and memory (not shown) to determine sample properties such as weight percent methane and GOR. The exemplary tool shown in FIG. 5 is fitted with ultraviolet, near infrared, mid-infrared (UV/NIR/MIR) wavelength light sources 112, which can be turned on when the tungsten light source 101 is turned off. The same spectrometer, comprising single wavelength filters 108 over spectrometer photodiodes, enables collecting the crude oil spectra for light transmitted, reflected or fluoresced in the UV, NIR, MIR bands associated the sample in flow channel 304.

The present invention provides a multiple channel spectrometer, in the current example comprising 24 channels of visible, near infrared (NIR) and mid infrared (MIR) light, which are shown through the sample 110 and filtered out into separate wavelength bands.

Two filters center wavelengths are carefully selected to be at 1670 nm and 1682 nm and to have bandpasses of 11 nm full width half maximum (FWHM). These two wavelengths were selected based on a complex simulation in which spectra of methane at various pressures and temperatures were added in random amounts to the spectra of 10 randomly chosen crude oil spectra from a data base of 500 spectra of diverse crude oil samples from around the world. The laboratory spectra were degraded to 11 nm resolution to approximate what is currently the best resolution of commercially available long-wavelength high temperature optical filters that are suitable for downhole use. Various step-forward and step-backward regressions with substitution were performed on the simulated mixtures over a wavelength region of 1500–1900 nm to determine the best-correlating center wavelengths, which turned out to be 1670 nm and 1682 nm, and their corresponding correlation equations. Temperature and pressure, which are non-optical parameters, were also used in the regressions along with the selected wavelengths to obtain the equation for weight fraction of methane.

According to the invention, a borehole apparatus for measuring the spectral peaks of a methane region includes a testing region, a conduit for directing formation fluid into the testing region, a light source emitting at least near infrared rays into the testing region, a spectral detector optically coupled to the testing region, and a processor coupled to the spectral detector. The testing region is a transparent cell or chamber, which is located between the light source and the spectral detector such that light directed from the light source to the spectral detector is interrupted by formation fluid. The spectral detector is preferably a spectrometer, which measures the spectrum of the light, which has been transmitted through the formation fluid in the testing region.

As shown in FIG. 6, the optimal center wavelengths 1670 nm and 1682 nm were derived from a regression analysis on a much broader wavelength region of 1500 nm–1900 nm. FIG. 6 illustrates the equations for calculation of methane weight and GOR from the selected channel measurements. FIG. 6 also shows empirical correlations developed for the weight fraction of methane in mixtures of methane and crude oil in the current example of the invention. The correlation equation gives the weight fraction of methane as a function of the mixture absorbance at two wavelengths (1670 nm and 1682 nm) and temperature. FIG. 6 also illustrates empirical correlations associated with the present invention and developed for the density of methane as a function of pressure and temperature and for the optical absorption per millimeter of methane as a function of methane density and wavenumber (a wavenumber is 10,000,000/wavelength expressed in nanometers) regardless of pressure and temperature.

As shown in FIG. 6, the equation for correlating weight fraction methane in mixtures of crude oil and methane to optical absorbance and temperature are illustrated.

The form of the equation for methane weight fraction in the present invention is that of an offset constant, B0, plus a first constant, B1, times a first variable, Var1, plus a second constant, B2, times a second variable, Var2, and so on to an N-th constant and variable.

METHWTF=Methane Weight Fraction=$B0+ B1*Var1+B2*Var2+B3*Var3+B4*Var4 \ldots BN*VarN$ The following is a first example of a Regression Summary for Dependent Variable: METHWTF $R=0.98093203$ $R^2 0.96222765$ Adjusted $R^2$ 0.96151158

$F(4,211)=1343.8$ $p<0.0000$ Std.Error of estimate: 0.04992

| | B |
|---|---|
| | 0.065139686 = B0 = Intercept |
| Var1 = SQ70_82 | 11.17561047 = B1 |
| Var2 = TEMP_C | 0.000869088 = B2 |
| Var3 = SRSA1682 | −2.661667658 = B3 |
| Var4 = SRSA1670 | 2.63244987 = B4 |

-continued

| B |
|---|
| Where: |
| SQ70_82 = SQUARE (Absorbance_at_1670_nm - Absorbance_at_1682_nm |
| SRSA1670 = SQRT (Absorbance_at_1670_nm |
| SRSA1682 = SQRT (Absorbance_at_1682_nm |
| TEMP_C = Temperature in Degrees Centigrade |
| TEMP_SQR = Square of Temperatire in Degrees C. |

The following is a second example of a Regression Summary for Dependent Variable: METHWT $R=0.98190316$ $R^2=0.96413381$ Adjusted $R^2=0.96327986$ $F(5,210)=1129.0$ $p<0.0000$ Std.Error of estimate: 0.04876

| | B |
|---|---|
| | 0.031427753 = B0 = Intercept |
| Var1 = SRSA1670 | 2.531111433 = B1 |
| Var2 = SRSA1682 | −2.557658783 = B2 |
| Var3 = SQ70_82 | 11.91350402 = B3 |
| Var4 = TEMP_C | 0.0019 = B4 |
| Var5 = TEMP_SQR | −6.2E−06 = B5 |

Baseline offset refers to a simultaneous and equal increase in the absorbance of whatever optical channels are being monitored. In this example, it would refer to an increase in the absorbance at both 1670 nm and 1682 nm by the same amount. Inspection of the first and second example equations shows that these equations have little sensitivity to baseline offset. This fact is one of the benefits of basing one's model on asphaltene-containing crude oils rather than on clear solvents. Doing so provides insensitivity to the presence of asphaltenes, which, to first order, simply appears as a baseline offset over the narrow wavelength region of 1670 nm to 1682 nm. The degree of this baseline offset depends upon the type of asphaltenes and upon their concentration.

The dominant term of the first equation is the square of the difference (the slope) between 1670 nm and 1682 nm. A slope is completely invariant to baseline offset. Also, taken together, the third and fourth terms are approximately equal to the slope between 1670 nm and 1682 nm on a plot of the square root of absorbance versus wavelength and so have low sensitivity to baseline offset. In like manner, the second equation is very insensitive to baseline offset and thus insensitive to the presence of asphaltenes, which inevitably are found in any real crude oil.

We developed the following empirical equation (Adjusted $R^2=0.99911359$) for the density of methane [g/cc] as a function of pressure and temperature from 100–30,000 psia and 75–200° C.

| | B |
|---|---|
| | 2.771E−03 = Intercept |
| P | 2.480E−05 |
| $P^2$ | −1.120E−09 for Pressure in psi |
| $P^3$ | 1.808E−14 |
| $T^2$ | −1.308E−07 for Temperature in C. |
| (P/T) | 1.455E−03 |

-continued

| | B |
|---|---|
| $(P/T)^2$ | −4.922E−06 |
| $(P/T)^3$ | 5.934E−09 |

We also developed the following empirical equation (Adjusted $R^2$=0.94145159) for optical absorbance per millimeter of methane as function of density and wavelength over 1668–1684 nm, 100–30,000 psia, and 75–200 C, assuming a bandpass of 11 nm FWHM.

| | B |
|---|---|
| | −19.9061 = Intercept |
| Methane Density | 0.7747 for Density in g/cc |
| WaveNumber/1000 | 3.3326 | where, Wavenumber=10,000,000/λ[nm]
The following definitions and equations let us relate GOR to Weight Fraction of
Methane, $f_M$, and Stock Tank Oil Density, $\rho_O$.
1 bbl=0.159 m$^3$=5.615 cu ft=42 U.S. gal
1 Standard Cubic Foot (SCF) of Methane Gas at the standard conditions of 14.7 psia and
60° F. is 0.042358 lbs=19.21327 grams.
So, the density of Methane at 60° F. and 14.7 psia is 0.0006787 gr/cc=0.042358 lbm/ft$^3$.
The Gas Oil Ratio is defined as $GOR = V_{Methane}[SCF]/V_{Oil}[bbls]$ so $GOR = \{W_M/(19.21 \text{ g/SCF})\}/\{(W_O/\rho_O)(1 \text{ bbl}/158\,983 \text{ cc})\}$ Let $f_M$=Weight Fraction of Methane, and let the subscripts V=Volume, W=Weight, ρ=Density, M=Methane, and O=Oil. Then:

$GOR = 8274.62 \, \rho_O/(1/f_M - 1)$ $f_M = W_M/(W_M + W_O) = \rho_M V_M/(\rho_M V_M + \rho_O V_O)$ or
$W_O = W_M/(1/f_M - 1)$.

Figure 7:
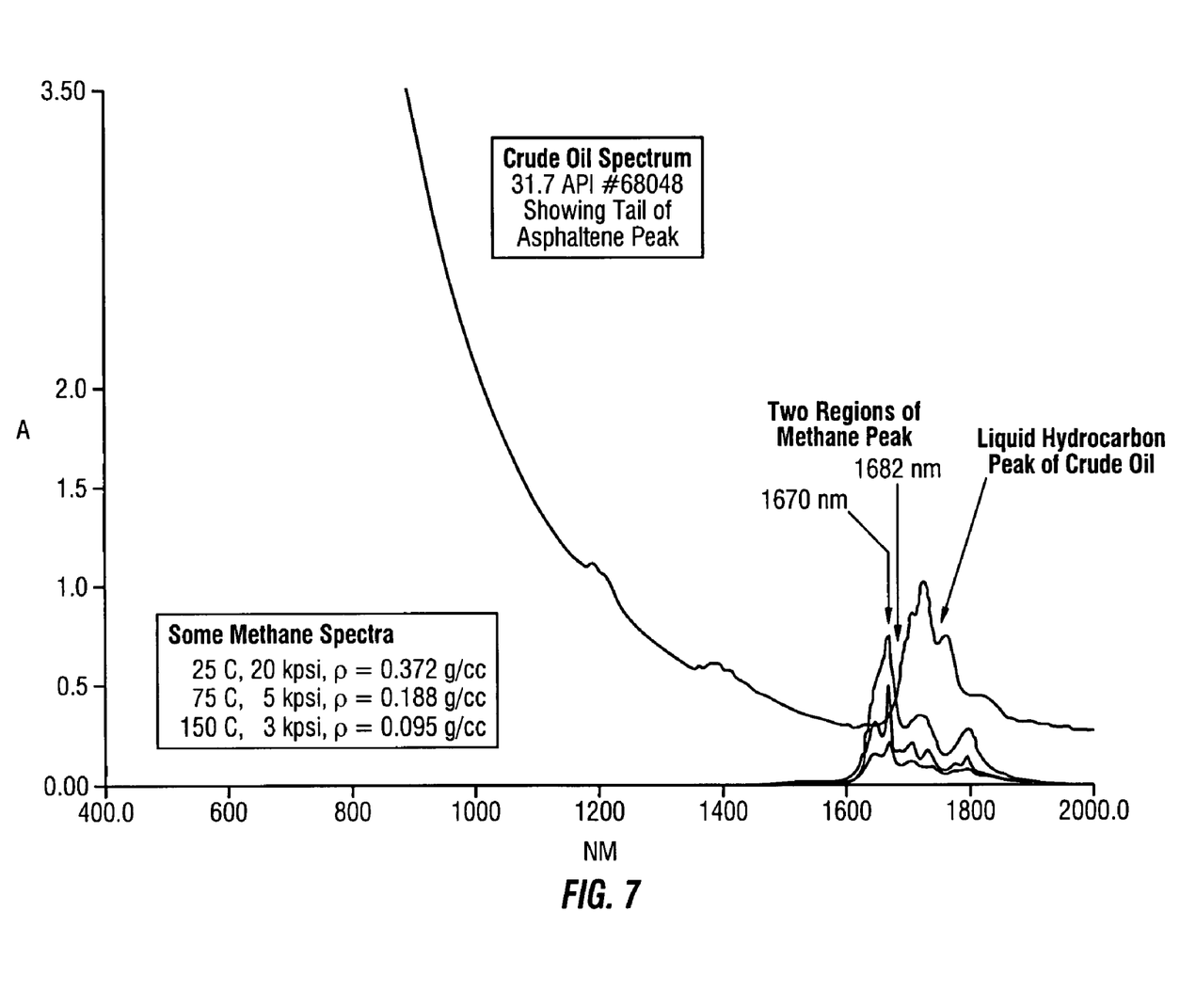
FIG. 7 illustrates three spectra of methane at various temperatures and pressures and one representative crude oil spectrum.

Rearranging the equation for GOR we obtain:

$f_M = 1/(1 + 8274.62 * \rho_O/GOR)$ where $W_G$ and $W_O$ are in grams, $\rho_O$ is in g/cc, and $f_M$=Wt. Frac. of Methane FIG. 7 shows three spectra of methane at various pressures and temperatures and the positions of the 1670 nm and 1682 nm channels relative to the methane peak. The higher the mass density [g/cc] of the methane the taller the methane peak. Note that the 1670 nm channel is almost at the pinnacle of the methane peak whereas the 1682 nm channel is slightly to the right of the pinnacle on the right shoulder of the methane peak.

Also shown is a representative crude oil spectrum. The rising left edge of this spectrum is the asphaltene peak of the crude oil. The liquid hydrocarbon peak of the crude oil is near 1740 nm. In a mixture of methane and crude oil, the methane peak will appear to sit on top of the right-hand tail of the asphaltene peak. That is why it is important that the weight-percent-methane model be insensitive to baseline offset.

Figure 8:
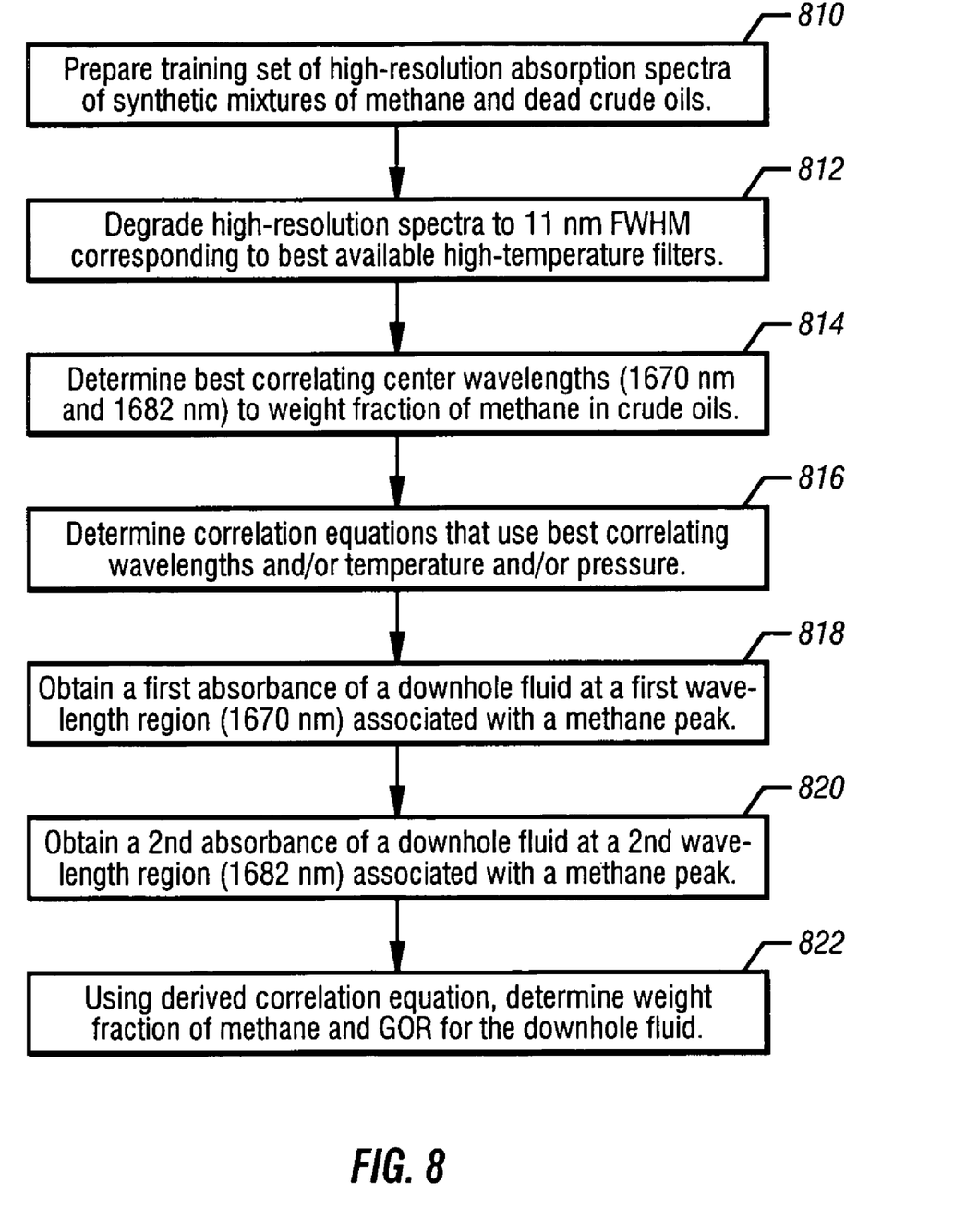
FIG. 8 illustrates a flow chart of functions performed by the present invention.

Turning now to FIG. 8, a diagram of some of the functions performed in the tool and associated processor functions in present example of the invention is illustrated. In block 810 in the present example of the invention a training set of high-resolution absorption spectra of synthetic mixtures of methane and dead crude oils is prepared. In block 812 in the present example of the invention these high-resolution spectra are degraded to 11 nm FWHM resolution corresponding to best available high-temperature filters. In block 814 in the present example of the invention the best correlating center wavelengths (1670 nm and 1682 nm) to weight fraction of methane in crude oils are determined. In block 816 in the present example of the invention the correlation equations that use these best correlating wavelengths and/or temperature and/or pressure are determined. In block 818 in the present example of the invention a first absorbance of a downhole fluid at a first wave-length region (1670 nm) associated with a methane peak is obtained. In block 820 in the present example of the invention a second absorbance of a downhole fluid at a second wave-length region (1682 nm) associated with a methane peak is obtained. In block 822 in the present example of the invention a weight fraction of methane and corresponding GOR for the downhole fluid are determined using the earlier derived correlation equation and the sample cleanup can be also monitored based on a change in weight percent methane or GOR.

The present invention has been described as method and apparatus operating in a downhole environment in the preferred embodiment, however, the present invention may also be embodied as a set of instructions on a computer readable medium, comprising ROM, RAM, CD ROM, Flash or any other computer readable medium, now known or unknown that when executed cause a computer to implement the method of the present invention. While a preferred embodiment of the invention has been shown by the above invention, it is for purposes of example only and not intended to limit the scope of the invention, which is defined by the following claims.

What is claimed is:

1. A method for quantifying a weight percent methane of a fluid downhole, comprising:
   obtaining the fluid downhole;
   measuring a first optical density for the fluid at a first wavelength region associated with a methane peak;
   measuring a second optical density for the fluid at a second wavelength region associated with the methane peak; and
   determining weight percent methane for the fluid sample from the first and second measured optical densities.

2. The method of claim 1, wherein the first wavelength region has a center wavelength of 1670 nanometers; and the second wavelength has a center wavelength of 1682 nanometers.

3. The method of claim 1, further comprising:
   correlating weight percent methane with optical absorbance at the first and second wavelengths.

4. The method of claim 3, further comprising:
   correlating pressure.

5. The method of claim 3, farther comprising:
   correlating temperature.

6. The method of claim further comprising:
   determining a gas oil ratio for the sample based on the weight percent methane.

7. The method of claim 1, further comprising:
   monitoring sample cleanup based on a change in weight percent methane.

8. The method of claim 3, further comprising:
   correlating based on synthetic mixtures of methane and dead crude oils.

9. The method of claim 1, further comprising:
filtering an optical density measurement with a 11 nm full width half maximum filter.

10. The method of claim 1, wherein the first wavelength region has a center wavelength of 1670 nanometers and the second wavelength has a center wavelength of 1662 nanometers;
correlating weight percent methane, pressure and temperature with optical absorbance at the first and second wavelength regions; and
determining a gas oil ratio based on the weight percent methane.

11. An apparatus for quantifying the weight percent of methane in a wellbore environment, comprising:
a tool for obtaining a fluid downhole;
a spectrometer for measuring a first optical density for the fluid at a first wavelength region associated with a methane peak and measuring a second optical density for the fluid at a second wavelength region associated with the methane peak; and
a processor function for determining weight percent methane for the fluid sample from the first and second measured optical densities.

12. The apparatus of claim 11, wherein the first wavelength region has a center wavelength of 1670 nanometers; and the second wavelength has a center wavelength of 1682 nanometers.

13. The apparatus of claim 11, further comprising:
a processor function for correlating weight percent methane with optical absorbance at the first and second wavelengths.

14. The apparatus of claim 13, the processor function further comprising a function for correlating pressure.

15. The method of claim 3, the processor function further comprising a function for correlating temperature.

16. The apparatus of claim 11 farther comprising:
a processor function for determining a gas oil ratio for the sample based on the weight percent methane.

17. The apparatus of claim 11, further comprising:
a processor function for monitoring sample cleanup based on a change in weight percent methane.

18. The apparatus of claim 13, the processor function further comprising a function for correlating based on synthetic mixtures of methane and dead crude oils.

19. The method of claim 11, further comprising:
a filter for filtering an optical density measurement with a 11 nm full width half maximum filter.

20. The apparatus of claim 11, wherein the first wavelength region has a center wavelength of 1670 nanometers and the second wavelength has a center wavelength of 1682 nanometers, the processor function further comprising a function for correlating weight percent methane, pressure and temperature with optical absorbance at the first and second wavelength regions and a function for determining a gas oil ratio based on the weight percent methane.

21. A computer readable medium in a computer containing executable instructions that when executed by a computer perform a method for quantifying the weight percent of methane in a wellbore environment, comprising;
obtaining a fluid downhole;
measuring a first optical density for the fluid at a first wavelength region associated with a methane peak;
measuring a second optical density for the fluid at a second wavelength region associated with the methane peak; and
determining weight percent methane for the fluid sample from the first and second measured optical densities.

22. The medium of claim 21, wherein the first wavelength region has a center wavelength of 1670 nanometers; and the second wavelength has a center wavelength of 1682 nanometers.

23. The medium of claim 21, further comprising:
correlating weight percent methane with optical absorbance at the first and second wavelengths.

24. The medium of claim 23, further comprising:
correlating pressure.

25. The medium of claim 23, further comprising;
correlating temperature.

26. The medium of claim 21 further comprising:
determining a gas oil ratio for the sample based on the weight percent methane.

27. The medium of claim 21, further comprising:
monitoring sample cleanup based on a change in weight percent methane.

28. The medium of claim 23, further comprising:
correlating based on synthetic mixtures of methane and dead crude oils.

29. The medium of claim 21, further comprising:
filtering an optical density measurement with a 11 nm full width half maximum filter.

30. The medium of claim 21, wherein the first wavelength region has a center wavelength of 1670 nanometers and the second wavelength has a center wavelength of 1682 nanometers; correlating weight percent methane, pressure and temperature with optical absorbance at the first and second wavelength regions; and determining a gas oil ratio based on the weight percent methane.

* * * * *